(12) United States Patent
Lootz

(10) Patent No.: US 6,596,021 B1
(45) Date of Patent: Jul. 22, 2003

(54) STENT

(75) Inventor: Daniel Lootz, Rostock (DE)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/695,453

(22) Filed: Oct. 24, 2000

(30) Foreign Application Priority Data

Oct. 26, 1999 (DE) .......................................... 199 51 475

(51) Int. Cl.$^7$ .................................................. A61F 2/06
(52) U.S. Cl. ...................................................... 623/1.16
(58) Field of Search .............................. 623/1.15, 1.16, 623/1.11, 1.12, 1.18, 1.32, 1.34

(56) References Cited

U.S. PATENT DOCUMENTS

| | | | |
|---|---|---|---|
| 4,655,771 A | 4/1987 | Wallsten | |
| 4,733,665 A | 3/1988 | Palmaz | |
| 4,739,762 A | 4/1988 | Palmaz | |
| 4,776,337 A | 10/1988 | Palmaz | |
| 4,964,126 A | 10/1990 | Wallsten | |
| 5,061,275 A | 10/1991 | Wallsten et al. | |
| 5,102,417 A | 4/1992 | Palmaz | |
| 5,104,404 A | 4/1992 | Wolff | |
| 5,195,984 A | 3/1993 | Schatz | |
| 5,755,781 A | 5/1998 | Jayaraman | |
| 5,843,175 A | 12/1998 | Frantzen | |
| 5,922,020 A | * 7/1999 | Klein et al. | 606/194 |
| 6,033,433 A | * 3/2000 | Ehr et al. | 623/1.16 |
| 6,071,308 A | 6/2000 | Ballou et al. | |
| 6,113,627 A | * 9/2000 | Jang | 623/1.49 |
| 6,261,319 B1 | * 7/2001 | Kveen et al. | 623/1.15 |

FOREIGN PATENT DOCUMENTS

| | | |
|---|---|---|
| DE | 297 08 689 U1 | 7/1997 |
| DE | 196 53 721 A1 | 4/1998 |
| EP | 0 335 341 B1 | 10/1992 |
| EP | 0 686 379 A2 | 12/1995 |
| EP | 0 792 627 A2 | 9/1997 |

* cited by examiner

Primary Examiner—David J. Isabella
Assistant Examiner—William H. Matthews
(74) Attorney, Agent, or Firm—Hahn Loeser & Parks LLP; Stephen L. Grant

(57) ABSTRACT

A stent, in particular a coronary stent, has at least one first tubular portion, and at least one second tubular portion. The first and second tubular portions are connected together by at least one first connecting means. The stent is distinguished in that the at least one first connecting means is in the form of a double bar.

15 Claims, 2 Drawing Sheets

STENT

Figure 1:
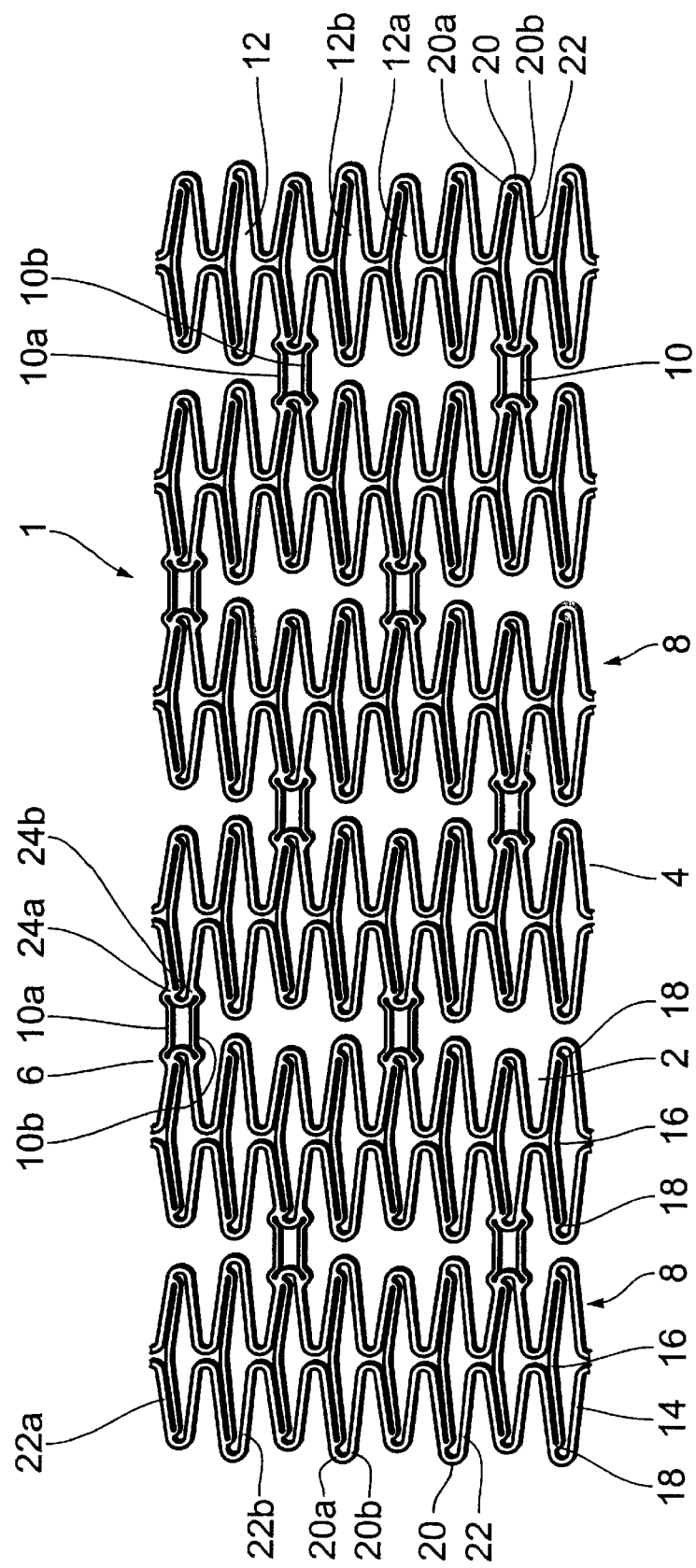

The invention concerns a stent, in particular a coronary stent, comprising at least one first tubular portion and at least one second tubular portion, wherein the first and second tubular portions are connected together by at least one first connecting means.

Stents of that kind are known from the state of the art in many different forms. Those stents are used inter alia in connection with percutaneous transluminal angioplasty (PCTA, Percutaneous Transluminal Balloon Angioplasty), in vascular surgery of the heart. Stents however can also serve to dilate other openings in the body or to keep such openings in a dilated condition. That medical procedure is initially preceded by determining the location of the constriction in a coronary blood vessel. A so-called angioplasty balloon is then moved in the artery which has the constriction, the so-called stenosis, to the location of the stenosis where it is inflated. Due to the radially outwardly directed force of the inflated balloon the constriction is dilated and in the optimum case the original passage cross-section of the previously constricted artery is restored. Besides successful dilation of the vessel however side-effects can also occur, which include local splits in the artery, disintegration effects and projections of plate portions and flakes into the lumen of the artery so that, in spite of the dilation effect, blockage of the vessel can still occur. In addition it is possible that a stenosis can recur due to the vessel wall elastically springing back and/or due to the growth of the intima of the vessel. Statistically, that occurs within six months in the case of over 30% of the patients who were treated with PCTA.

In order now immediately after dilation of the blood vessel to ensure a relatively smooth inside wall surface for the vessel and to be able to avoid renewed stenosis, the stents set forth in the opening part of this specification were developed. Those small tubes serve inter alia in conjunction with PCTA to maintain the vessel flow cross-section which is produced by balloon angioplasty in order thereby to ensure long-term success with the PCTA procedure.

The success of such so-called stenting also depends inter alia on how uniformly the stent can come to bear against the wall of the vessel. For, the more uniformly the wall of the vessel is supported, the correspondingly more probable it is that vessel constrictions will not recur in the region of the stent. In that respect a regular stent structure produces a relatively smooth inside surface for the vessel and, with a relatively smooth inside vessel surface, blood particles can only be deposited thereon with difficulty. In addition growths of the intima into the interior of the vessel are prevented to a greater degree by a regular stent structure which covers over the inside surface of the vessel in a relatively closed configuration.

Stents of that kind with a so-called closed structure are also known from the state of the art. By way of example reference may be made here to one of the best-known stents of that kind, the so-called wall stent. That is known for example from U.S. Pat. No. 4,65,771. This stent which has a closed structure is formed from two wires which are regularly knitted in a mesh-like structure and which extend in a spiral configuration on the longitudinal axis of the stent.

The advantage of the closed structure of stents of that kind is however only achieved at the cost of the disadvantage that the stents involve relative longitudinal stiffness during insertion. Those stents do not therefore make it possible in the optimum manner for the stent to be guided through possibly very severely curved vessel portions in the coronary arteries upon insertion in a direction towards the stenosis to be treated. Those longitudinally stiff stents also cannot be used in the region of curvy vessel portions. In order to avoid those disadvantages of a closed structure, stents have now been developed which are of a so-called modular nature. In the case of those stents of a modular nature, individual portions which are provided with a closed structure are connected together by flexible connections. Stents of that kind are known for example from U.S. Pat. No. 5,104,404.

A disadvantage with the known modular or segmented stents however is that upon crimping of the stent (the term crimping is used to denote mounting the stent on the balloon catheter in a non-displaceable fashion by applying a gentle, radially inwardly directed pressure thereto), the stent may involve a non-uniform behavior. For, in the crimping operation the tubular portions exhibited a different behavior from the individual bars which serve as connecting means, between the tubular portions. In addition there is the disadvantage with the known stents for precisely those reasons that the stent also entails a non-uniform expansion characteristic. With that non-uniform expansion of the known stents the stent may involve inter alia a radial spreading movement of individual bars. That spreading movement is unwanted however as it interrupts the uniformity, which has already been referred to above, of the inside wall of the expanded stent. In addition that can also involve injury and damage to the intima of the stented vessel. In addition, in the case of conventional stents which are composed of various segments, expansion of the stent can involve the stent expanding in a shape referred to as a "dog-bone" shape. In that situation, the tubular portions which are at the ends of the stent are expanded to a greater degree than the tubular portions which are more in the central region of the stent. That is also disadvantageous for the above-discussed reasons, in particular in regard to durably suppressing further deposits on the inside wall of the stent.

Therefore the object of the present invention is to further develop a stent of the kind set forth in the opening part of this specification, in such a way that the above-mentioned disadvantages are avoided, and that there is made available a stent in which the flexural flexibility of segmented stents or stents which are also referred to as modular is maintained while at the same time the longitudinal stability of the stent is increased.

In a stent of the kind set forth in the opening part of this specification that object is attained in that the at least one first connecting means is in the form of a double bar.

By means of the double bar according to the invention the invention achieves a longitudinal stability for the stent which is markedly increased in comparison with conventional segmented stents while at the same time the flexural flexibility of the modular design of the stent is maintained. In that way by virtue of the invention it is possible for the stent not to be compressed during balloon dilation. In addition, because of the invention, the adjacent tubular portions cannot come into unwanted contact with each other. In that way, by means of the invention, adjacent tubular portions are prevented from influencing each other upon expansion of the stent in the balloon dilation procedure. In addition, the double bars according to the invention, in contrast to the single bars known from the state of the art, provide as a connecting means between the adjacent tubular portions for a more regular and uniform crimping and expansion behavior on the part of the stent. In that case the invention advantageously avoids inter alia radial spreading of bars upon balloon dilation and also prevents the tubular portions at the ends of the stents from expanding in a "dog-bone" configuration.

A particularly preferred embodiment of the invention is distinguished in that the tubular portions each comprise a plurality of cells, wherein the double bar according to the invention connects together cells, which are adjacent in the longitudinal direction of the stent, of the respective portions. This cell-type structure of the tubular portions provides for an optimum expansion behavior on the part of the stent upon expansion thereof.

In a further preferred embodiment the portions are formed from identical cells which are arranged in adjacent relationship in the peripheral direction. That advantageously affords a crimping and expansion behavior on the part of the stent, which is uniform and regular in the peripheral direction.

In a further preferred embodiment the cells of adjacent portions are of identical structure. In that case, it is preferred if all cells of all portions are of identical structure, in which respect it is particularly further preferred if all portions are also of identical structure. In this embodiment, that affords a completely uniform and regular crimping and expansion behavior on the part of the stent according to the invention over the entire length thereof.

In a particularly preferred embodiment of the invention the cells of the portions are each constructed from 2 mutually facing closed bars which extend in a meander configuration in the peripheral direction of the portions and which are connected together to form the cells by means of second connecting means which are in the form of single bars. Closed bars of that kind implement the object according to the invention of maintaining flexural flexibility with at the same time longitudinal stability of the stent in a particularly advantageous fashion as, in this embodiment, the double bars according to the invention can extend between the meander-shaped bars insofar as they engage the upper or lower apex points of the bar meander which extends in the peripheral direction, depending on the demands on the stent. At the same time optimally uniform expansion of the stent becomes possible by virtue of the meander-shaped boundary of the tubular portions.

In a further preferred embodiment of the invention the meander bars are arranged in mirror image-symmetrical relationship on the periphery. In that way in particular the arcuate portions of the meander-shaped bars, which extend outwardly with respect to the mirror-image plane, are used to form the cells of the tubular portions.

In that case it is further preferred if the meander shape of the meander bars substantially corresponds to the configuration of a sine curve along a peripheral line of the tubular portions. That ensures a particularly harmonic expansion behavior on the part of the stent according to the invention as a bar which is curved in a sinusoidal configuration expands in a particularly uniform manner upon expansion of the stent.

In a further preferred embodiment of the invention each second arcuate portion of the bars which are of a sinusoidal meander configuration in the peripheral direction of the tubular portions is flatter than the remaining arcuate portions. That arrangement provides that the cells of the tubular portions, which are enclosed by the meander bars, are also alternately of a varying size. This embodiment provides that the stent according to the invention, even when being introduced into curved or bent vessels, enjoys a sufficiently large free motion between the tubular portions. That free motion or freedom of movement between the tubular portions which is afforded by virtue of the flatter arcuate portions of the bars thus ensures that adjacent tubular portions do not hinder each other or hook one into the other upon bending of the stent. It is further preferred in this embodiment if the double bar or bars connects or connect the tubular portions at locations at which the flatter arcuate portions of the meander bars are provided. In that way upon bending of the stent the stent enjoys a particularly great free motion between the tubular portions so that the above-mentioned advantages are still further enhanced.

In a further particularly preferred embodiment of the invention the apex points of the substantially sinusoidal arcuate portions of the meander bars are of a flattened configuration in the longitudinal direction of the tubular portions. In this embodiment therefore the reversal points of the meanders are provided with double radii. In this embodiment that advantageously ensures that the arcuate portions of the meander configurations do not spread apart in a "donkey's ear" fashion. That in turn advantageously prevents the intima of the vessel suffering from damage and injury which is linked to such a spreading movement.

In that respect this embodiment also generally provides for a more regular crimping and expansion characteristic on the part of the stent. Furthermore, the mechanical loadings on a coating which is preferably provided on the stent surface, that is to say on the bars, are reduced by virtue of the flattened apex points or by the double radii of the meander reversal points. For, due to the double radii involved, upon expansion of the stent the loading on the coating or the loading on the adhesion of the coating to the bar surface is exerted not just on a reversal point in the meander configuration but on the two portions, formed by the double radii, of the reversal or apex points of the meander configurations. Therefore that distribution of the deformation of the meander configurations upon expansion of the stent over the two radius portions of the arcuate configurations of the meanders overall advantageously reduces the loading on the coating on a stent.

A further preferred embodiment of the invention is distinguished in that the second connecting means respectively connect regions of the meander bars which are arranged in adjacent relationship in the longitudinal direction of the tubular portions. In that case it is further preferred if the second connecting means connect two meander bars respectively in the proximity of their regions which are at the maximum longitudinal spacing. In that arrangement the second connecting means which are in the form of single bars preferably extend substantially in the longitudinal direction of the tubular portions. Thus, this embodiment advantageously provides for a minimization in the contraction in respect of length of the stent upon expansion thereof. Those longitudinal bars also serve for lengthwise stabilization of the stent. In that respect those longitudinal bars advantageously co-operate with the double bars according to the invention in regard to lengthwise stabilization of the stent.

In a further particularly preferred embodiment the ends of the second connecting means which are in the form of single bars extend substantially in the peripheral direction of the tubular portions. In this case, in a further preferred embodiment, alternatively thereto or in addition thereto, the single bars may taper towards their respective connecting point to the meander bars.

Then in that way the single bars which serve as the second connecting means form yield hinges or pivots between the meander bars. Those yield hinges advantageously ensure that the radial expansion characteristic of the stent upon expansion thereof is influenced to the minimum possible degree.

In a further advantageous development of the present invention the ends of the double bars are mounted to locations on the meander bars, in the immediate proximity of which the single bar of the second connecting means, which is longitudinally adjacent along the respective tubular portion, is also fixed. In this embodiment, that provides for maximum possible longitudinal stability of the stent, insofar as both bars which extend in the longitudinal direction of the stent, that is to say the double bar and the single bar, extend substantially in mutually aligned relationship in the longitudinal direction.

Further preferred embodiments of the invention are set forth in the appendant claims.

Figure 3:
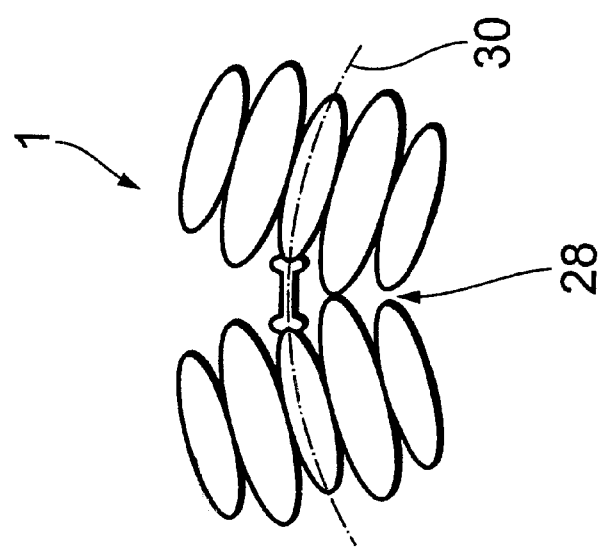
Figure 2:
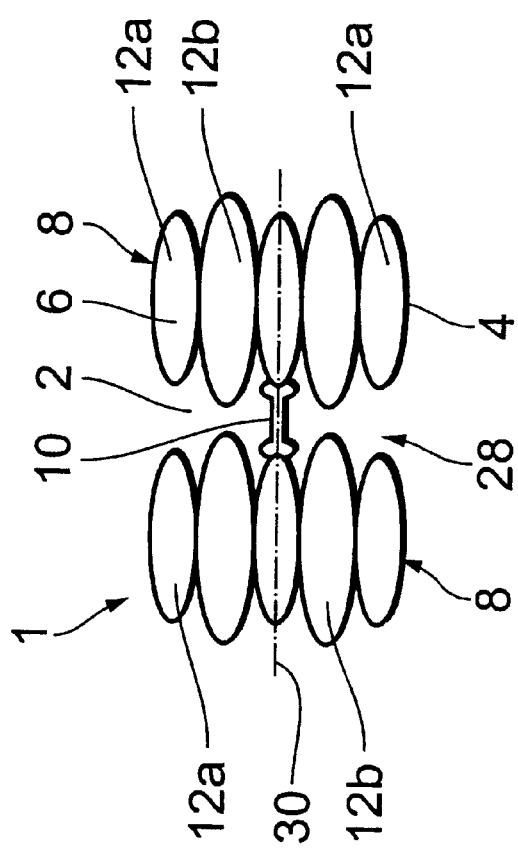

Two advantageous embodiments of the invention are now described with reference to the accompanying drawings in which:

FIG. 1 shows a stent according to the invention which is illustrated by reference to the development of its peripheral surface, FIG. 2 diagrammatically shows a second embodiment of a stent according to the invention by reference to the development of the peripheral surface thereof, and FIG. 3 shows the embodiment of FIG. 2 with the stent in a bent condition.

FIG. 1 shows a stent 1 according to the invention. The stent 1 is shown in FIG. 1 as a development of the peripheral surface 2 of the stent 1. When the stent 1 is in the condition of being ready for operation, the peripheral surface 2 is joined together with its side 4 which is shown at the bottom in FIG. 1 to the side 6 which is shown at the top in FIG. 1, thereby affording the operable stent 1

The peripheral surface 2 is composed of six tubular portions 8. It will be appreciated that those tubular portions 8 are not tubular in the development of the peripheral surface 2 as in shown in FIG. 1. The tubular configuration of the tubular portions 8 is only achieved by the sides 4 and 6 of the peripheral surface 2 being joined together as indicated above.

In the longitudinal direction which extends from left to right in the plane of the drawing in FIG. 1 the tubular portions 8 are connected together by double bars 10 serving as connecting means according to the invention.

In addition the tubular portions 8 are made up from a plurality of cells 12 arranged in adjacent relationship in the peripheral direction of the stent 1. The cells 12 of the tubular portions 8 are alternately of a different size. There are however only two differently sized cells 12 in the entire stent 1 or in the peripheral surface 2 of the stent 1. The cells 12 involve the smaller cells 12a and the larger cells 12b.

All portions 8 are of an identical configuration relative to each other and therefore involve the same sequence of smaller cells 12a and larger cells 12b.

The cells 12 are respectively formed in each tubular portion 8 by two mutually facing closed bars 14 which extend in a meander configuration in the peripheral direction of the tubular portions 8. The bars 14 are in turn connected together in paired relationship by means of single bars 16 which extend substantially in the longitudinal direction and which serve as second connecting means according to the invention. Those single bars 16 are thicker at their centers than at their ends 18. The bars 16 therefore narrow or taper towards their ends 18. In addition the ends 18 of the bars 16 are bent substantially in the peripheral direction towards the side 6 of the peripheral surface 2, which side is shown at the top in FIG. 1, before they are then fixed to the bars 14.

The bars 14 of a meander configuration have a meander which extends in a substantially sinusoidal shape. In this case however the respective apex points 20 of the arcuate portions 22 of the bars 14 are flattened, that is to say they are provided with double radii. That therefore affords two partial regions 20a and 20b which respectively form the partial radii of the arcuate portions 22. The individual bars 16 which connect the bars 14 together are all mounted in the region of the partial radii 20a of the arcuate portions 22.

The sinusoidal meander shape of the bars 14 extends alternately irregularly insofar as the arrangement involves large arcuate portions 22b and small arcuate portions 22a. In that way the small cells 12a are formed by the small arcuate portions 22a and the large cells 12b of the tubular portions 8 are formed by the large arcuate portions 22b.

The double bars 10 according to the invention are formed from two single bars 10a and 10b which extend in substantially parallel relationship. The double bars 10 always respectively connect the tubular portions 8 at small cells 12a which are in adjacent relationship with each other. Each two tubular portions 8 are connected together by two double bars 10. In this case the double bars 10 are arranged in such a way that three pairs of cells of tubular portions 8 are disposed between the double bars. In addition the double bars 10 are arranged in mutually displaced relationship in such a way that the second pair of tubular portions which is beside a first pair is connected together by the double bars 10 at locations which are arranged in displaced relationship with respect to the connecting locations of the first pair of tubular portions 8, in such a way that a respective pair of large cells 12b is disposed between each two connecting locations.

The single bars 10a and 10b of the double bars 10 are initially bent away at their ends from their fixing points 24a and 24b respectively in the direction of a first diagonal of the peripheral surface 2, and are then directly bent towards the bars 14 in the direction of the second diagonal of the peripheral surface 2 in the immediate proximity of the fixing points 24a and 24b to the bars 14. The fixing points 24a and 24b are respectively disposed in the region of the partial radii 20a and 20b of the smaller arcuate portions 22a. In addition the fixing points 24a of the single bars 10a of the double bars 10, which single bars are shown at the top in FIG. 1, are arranged in the immediate proximity of the single bars 16 arranged in the corresponding cells 12.

FIG. 2 shows a diagrammatic view of the peripheral surface 2 of a second embodiment of the stent 1 according to the invention. Parts which correspond to those shown in FIG. 1 are denoted by the same references.

Two diagrammatically illustrated tubular portions 8 are connected together by a diagrammatically illustrated double bar 10. The tubular portions 8 have small cells 12a and large cells 12b. By virtue of the choice of the length of the double bar 10 and the choice of the extent of the cells 12a and 12b extending in the direction of the longitudinal axis 30, a free space 28 is formed between the small cells 12a of the tubular portions 8, which are disposed outwardly at the sides 6 and 4 respectively of the peripheral surface 2.

FIG. 3 shows the embodiment of FIG. 2 in a condition in which the stent 1 is bent. That bending of the stent 1 is diagrammatically indicated by the bent dash-dotted longitudinal line 30 illustrated in the Figure. FIG. 3 shows that the free motion space 28 is almost completely utilized in the flexural motion shown in FIG. 3.

What is claimed is:

1. A stent having longitudinal and peripheral directions comprising:

at least one fist tubular portion; and at least one second tubular portion;

wherein each said first and second tubular portion comprises:

a plurality of cells arranged in adjacent relationship in the peripheral direction;

wherein the plurality of cells comprises two meander bars that are mutually facing closed bars that extend in a substantially sinusoidal meander configuration in the peripheral direction, the two meander bars joined by a plurality of single bar connectors extending substantially in the longitudinal direction;

each of the meander bars comprising a plurality of first arcuate portions and second arcuate portions, with the first and second arcuate portions joined in alternating fashion, with each second arcuate portion longer in the longitudinal direction than the first arcuate portions; and at least one double bar connector connecting cells of each first tubular portion to cells of a longitudinally-adjacent second tubular portion.

2. The stent of claim 1 wherein each of the at least one first and second tubular portions have an identical structure.

3. The stent of claim 1 wherein the meander bars are formed in mirror image-symmetrical relationship with respect to a peripheral line of the tubular portion formed thereby.

4. The stent of claim 3 wherein the single bar connectors connect regions of the meander bars, which regions are respectively arranged in adjacent relationship in the longitudinal direction of the tubular portions.

5. The stent of claim 4 wherein the single bar connectors connect two respective meander bars in the proximity of their regions which are at a maximum spacing in the longitudinal direction of the tubular portions.

6. The stent of claim 5 wherein the single bar connectors extend substantially in the longitudinal direction.

7. The stent of claim 6 wherein the ends of the single bar connectors extend substantially in the peripheral direction.

8. The stent of claim 7 wherein the single bar connectors connect the meander bars at points of minimum deformation of the meander bars upon expansion of the stent.

9. The stent of claim 8 wherein the single bar connectors narrow towards their ends.

10. The stent of claim 9 wherein the double bar connectors extend substantially in the longitudinal direction.

11. The stent of claim 10 wherein each of the at least one double bar connectors has first and second ends that extend substantially in the peripheral direction.

12. The stent of claim 11 wherein the at least one double bar connectors connect together the tubular portions proximate to a smallest mutual longitudinal spacing of the tubular portions.

13. The stent as set forth in claim 1 wherein the at least one double bar connectors are attached to the meander bars proximate to a location at which the single bar connector is also fixed to said meander bars.

14. The stent of claim 1 wherein each of the plurality of the cells in each of the at least one first tubular portions has an identical structure to a corresponding cell in the plurality of cells in the each of the at least one adjacent second tubular portions.

15. The stent of claim 14 wherein the plurality of cells comprise small cells and large cells which alternate in the peripheral direction, each said double bar connector joining one of the small cells on the first tubular portion to one of the small cells on the adjacent second tubular portion.

* * * * *